United States Patent [19]

Duff et al.

[11] Patent Number: 4,937,164
[45] Date of Patent: Jun. 26, 1990

[54] THIONATED PERYLENE PHOTOCONDUCTIVE IMAGING MEMBERS FOR ELECTROPHOTOGRAPHY

[75] Inventors: James M. Duff; Ah M. Hor; Cheng K. Hsiao; Gordon K. Hamer, all of Mississauga; Rafik O. Loutfy, Willowdale, all of Canada

[73] Assignee: Xerox Corporation, Stamford, Conn.

[21] Appl. No.: 373,126

[22] Filed: Jun. 29, 1989

[51] Int. Cl.$^5$ .............................................. G03G 5/14
[52] U.S. Cl. .......................................... 430/58; 585/26
[58] Field of Search ............................................ 430/58

[56] References Cited

U.S. PATENT DOCUMENTS

| | | | |
|---|---|---|---|
| 4,028,102 | 6/1977 | Rochlitz et al. | 430/57 |
| 4,399,207 | 8/1983 | Sakai et al. | 430/58 |
| 4,454,211 | 1/1984 | Takasu et al. | 430/59 |
| 4,554,231 | 11/1985 | Tshikawa et al. | 430/59 |
| 4,587,189 | 5/1986 | Hor et al. | 430/59 |
| 4,714,666 | 12/1987 | Wiedemann et al. | 430/59 |

Primary Examiner—J. Davis Welsh
Attorney, Agent, or Firm—E. O. Palallo

[57] ABSTRACT

A photoresponsive imaging member comprised of a thionated perylene photogeneratoring layer, and a charge transport layer.

30 Claims, 6 Drawing Sheets

THIONATED PERYLENE PHOTOCONDUCTIVE IMAGING MEMBERS FOR ELECTROPHOTOGRAPHY

BACKGROUND OF THE INVENTION

This invention is generally directed to layered photoresponsive imaging members, and more specifically to photoconductive members comprised of thionated perylene compounds. In one embodiment of the present invention, there are provided organic photoconductive layered imaging members comprised of certain thionated perylene compounds and charge or hole transport layers comprised of, for example, aryl amines as illustrated in U.S. Pat. No. 4,265,990 and copending application U.S. Ser. No. 215,099, the disclosures of which are totally incorporated herein by reference. Further, in one important embodiment of the present invention there is provided a photoresponsive imaging member or device comprised of thionated perylenes of the formulas illustrated herein, and the derivatives thereof, and an aryl amine hole transport layer. The photoresponsive imaging members of the present invention can be selected for various electrophotographic imaging and printing processes, especially xerographic processes wherein, for example, latent images are formed thereon followed by development and transfer to a suitable substrate.

Illustrated in U.S. Pat. No. 4,315,981 are organic doulbe layered electrophotographic recording materials consisting of an electroconductive support with a photoconductive double layer of organic materials, which consist of a homogeneous opaque charge carrier producing dyestuff layer obtained from an annealed quinone, or the substitution product thereof selected from the group consisting of dibenzoyrenequinone, anthraquinone, pyranthrone, dibenzathrone, and flavanthrone, and a transparent top layer of insulating materials of at least one charge transporting compound, which transport layer consists of a charge transporting monomer, reference for example column 2, lines 37 to 56. Further, as indicated in column 4, lines 1 to 22, as the formula 9 compound for the imaging member of the '981 patent there can be selected dibromo-8,16-pyranthrenedione (Indanthrene Orange RRTS, C.I. 59,705). Moreover, it is indicated in column 4, beginning at around line 53, that the organic dyestuff layer may be applied by vapor depositing the dyestuff in a vacuum. Also, this patent discloses a number of resinous binders for the charge transport layer including polycarbonate resins, reference column 7. Further, in U.S. Pat. No. 3,871,882 there are disclosed layered electrophotographic recording materials containing an electroconductive support material and a photoconductive double layer of organic materials, reference for example the Abstract of the Disclosure.

In Konishiroku Kokai Japanese 59/184349/A2[84/184349], 19 Oct. 1984, there is disclosed the use of selected pyranthrones as charge generator layers in conjunction with hydrazone charge transport layers. Specifically, a solution coated dispersion of dibromo-8,16-pyranthrenedione in a polymer binder can be selected as the charge generator layer. Also, in U.S. Pat. No. 3,877,935 there are disclosed imaging members with dibromo-8,16-pyranthrenedione vacuum coated charge generator layers contiguous with poly(-vinyl carbazole) charge transport layers.

As a result of a patentability search, there were selected U.S. Pat. Nos. 4,028,102; 4,399,207; 4,454,211; 4,554,231 and 4,714,666. In the '102 patent, there is illustrated diamine condensation products in double layered photoconductive recording elements. More specifically, there is disclosed in the '102 patent condensation products of o-phenylene diamine or 1,8-diaminonaphthalene and 4,10-benzothioxanthrene-3,1'-dicarboxylic anhydride of the formulas as illustrated in column 2, and of the formulas 1 to 5, reference column 3, beginning at line 55. The '207 patent discloses electrophotographic photosensitive members with hydrazone compounds of the formula, for example, as illustrated in the Abstract of the Disclosure and in column 2. Examples of charge generating layer materials are illustrated beginning in column P16, line 65, and include, for example, phthalocyanine pigments, perylene pigments, and the like, typical examples of which are specifically recited in columns 17 through 26. The '211 patent discloses electrophotographic photosensitive members with pyrazoline charge transport materials, see for example column 2, beginning at line 35. Specific organic photoconductive materials or charge transporting materials for use in the invention of the '211 patent are illustrated according to the teachings thereof in columns 3 and 4, formulas 1 and 2, of the '211 patent. Charge generating layers for the photoconductive members in the '211 patent are illustrated in column 42, beginning at line 11, and include, for example, organic substances such as pyrylium dyes, thiopyrylium dyes, perylene pigments, and the like with specific examples of charge generating materials being illustrated in columns 42 to 52. Also, it is disclosed in column 57 that a charge generating layer can be formed on an aluminum plate by the vacuum deposition of a perylene pigment having carbon atom bridges at the 1, 12 and 6, 7 positions of the common perylene molecule. In U.S. Pat. No. 4,554,231, there is illustrated an electrophotosensitive member comprised of a layer containing a hydrazone compound of the formula, for example, as illustrated in the Abstract of the Disclosure, which hydrazone compound is selected as charge transport material, reference column 5, line 30, and wherein there are selected various charge generating layer materials including, for example, pyrylium dyes, thiopyrylium dyes, perylene pigments and the like, see column 6, beginning at line 23, and note particularly columns 7 through 12. The use of Vylon 200 on a charge generating layer is disclosed at column 19, lines 15 to 21, and according to the searcher, there is shown at the bottom of column 12 a perylene molecule which may be used, which includes a two carbon atom bridge at both the 1, 12 and 6, 7 positions of a perylene molecule. In the 4,714,666 patent, there are illustrated perylene tetracarboxylic acid imide pigments in electrophotographic recording materials, which pigments include those, for example, as represented by the formula 1, reference the Abstract of the Disclosure.

Moreover, in U.S. Pat. No. 4,587,189, the disclosure of which is totally incorporated herein by reference, there are illustrated layered imaging members with photoconductive layers comprised of cis and trans-bis(-benzimidazo)perylene pigments.

Additionally, numerous different xerographic photoconductive members are known including, for example, a homogeneous layer of a single material such as vitreous selenium, or a composite layered device containing a dispersion of a photoconductive composition. An example of one type of composite xerographic photoconductive member is described, for example, in U.S. Pat. No. 3,121,006 wherein there is disclosed finely divided particles of a photoconductive inorganic compound dispersed in an electrically insulating organic resin binder.

There are also known photoreceptor materials comprised of inorganic or organic materials wherein the charge carrier generating, and charge carrier transport functions are accomplished by discrete contiguous layers. Additionally, layered photoreceptor materials are disclosed in the prior art which include an overcoating layer of an electrically insulating polymeric material. However, the art of xerography continues to advance and more stringent demands need to be met by the copying apparatus in order to increase performance standards, and to obtain quality images. Also, there have been disclosed other layered photoresponsive devices including those comprised of separate generating layers, and transport layers as described in U.S. Pat. No. 4,265,990, the disclosure of which is totally incorporated herein by reference. Examples of photogenerating layers disclosed in this patent include trigonal selenium and phthalocyanines, while examples of transport layers include certain diamines as mentioned herein.

Many other patents are in existence describing photoresponsive devices including layered devices containing generating substances, such as U.S. Pat. No. 3,041,167 which discloses an overcoated imaging member containing a conductive substrate, a photoconductive layer, and an overcoating layer of an electrically insulating polymeric material. This member is utilized in an electrophotographic copying system by, for example, initially charging the member with an electrostatic charge of a first polarity, and imagewise exposing to form an electrostatic latent image, which can be subsequently developed to form a visible image.

Furthermore, there are disclosed in U.S. Pat. Nos. 4,232,102 and 4,233,383 photoresponsive imaging members comprised of trigonal selenium doped with sodium carbonate, sodium selenite, and trigonal selenium doped with barium carbonate, and barium selenite, or mixtures thereof. Moreover, there are disclosed in U.S. Pat. No. 3,824,099 certain photosensitive hydroxy squaraine compositions. According to the disclosure of this patent, the squaraine compositions are photosensitive in normal electrostatographic imaging systems.

In U.S. Pat. No. 4,508,803, the disclosure of which is totally incorporated herein by reference, there is described an improved photoresponsive device comprised of a supporting substrate, a hole blocking layer, an optional adhesive interface layer, an inorganic photogenerating layer, a photoconducting composition layer comprised of benzyl fluorinated squaraine compositions, and a hole transport layer. Other representative patents disclosing photoconductive devices with squaraine components therein include U.S. Pat. No. 4,507,408; 4,552,822; 4,559,286; 4,507,480; 4,524,220; 4,524,219; 4,524,218; 4,525,592; 4,559,286; 4,415,639; 4,471,041 and 4,486,520. The disclosures of each of the aforementioned patents are totally incorporated herein by reference.

Moreover, disclosed in the prior art are composite electrophotographic photosensitive materials with various azo compounds. For example, there is illustrated in Japanese Ricoh Patent Publication 6064354, published Apr. 12, 1985, composite photoconductors wherein one of the photoconductor layers contains an azo compound of the formulas as illustrated. Further, there are illustrated in several U.S. patents and publications layered organic electrophotographic photoconductor elements with azo, bisazo, or related compounds. Examples of these patents and publications include U.S. Pat. No. 4,400,455; 4,551,404; 4,390,608; 4,327,168; 4,299,896; 4,314,015; 4,486,522; 4,486,519 and 4,551,404; and Konishiroku Japanese Patent Laid Open Publication 60111247.

Other prior art that may be of background interest includes Japanese Pat. No. 59-59686; Japanese Pat. No. 59-154454; European Pat. No. 100,581; U.S. Pat. No. 4,578,334; European Pat. No. 40,402;. U.S. Pat. No. 4,431,721; German Pat. No. 3,110,954; R. O. Loutfy, Can. J. Chem 59, 544, (1981); and F. Graser and E. Hadicke, Liebigs Ann. Chem., 483 (1984).

Although photoconductive imaging members are known, there remains a need for members with other photogenerator layers. Additionally, there continues to be a need for layered photoresponsive imaging members having incorporated therein thionated perylene compounds, which members will enable the generation of acceptable high quality images and wherein these members can be repeatedly used in a number of imaging cycles without deterioration thereof from the machine environment or surrounding conditions. Moreover, there is a need for improved layered photoresponsive imaging members wherein the thionated perylene compounds selected for one of the layers in combination with specific aryl amine charge transport compositions are substantially inert to the users of such members. Additionally, there is an important need for layered photoconductors with thionated perylene compounds, which photoconductors are of high sensitivity, have low dark decay values, low residual potentials, and possess high cyclic stability. Furthermore, there continues to be a need for photoresponsive imaging members which can be positively or negatively charged thus permitting the development of images, including color images with positively or negatively charged toner compositions. Also, there is a need for disposable imaging members useful in xerographic imaging processes, and xerographic printing systems wherein, for example, light emitting diodes (LED), helium cadmium or helium-neon lasers, solid state AlGaAs diode lasers, can be selected; and wherein these members are particularly sensitive to the visible and near infrared region of the spectrum, that is from about 400 to about 700 nanometers.

SUMMARY OF THE INVENTION

It is therefore an object of the present invention to provide photoresponsive imaging members with many of the advantages illustrated herein.

A further object of the present invention is the provision of improved economical photoconductive imaging members comprised of thionated perylenes with high photosensitivity, low dark decay values, and excellent cyclic stability.

Another object of the present invention resides in the provision of organic layered photoconductive imaging members containing therein certain thionated perylene compounds as photogenerating layers and aryl amine hole transport layers.

In yet another specific object of the present invention there are provided negatively charged layered photoresponsive imaging members comprised of certain thionated perylene compounds optionally dispersed in a resinous binder, and in contact therewith a hole transport layer comprised of aryl amine molecules.

There are provided in another object of the present invention positively charged layered photoresponsive imaging members with a top photogenerating layer comprised of thionated perylene photogenerating pigments optionally dispersed in a resinous binder, and thereunder a hole transport layer comprised of aryl amine molecules.

Further, in yet another object of the present invention there are provided imaging and printing methods with the improved photoresponsive imaging members illustrated herein.

Also, in a further important object of the present invention there are provided improved imaging members sensitive to light in the visible region of the spectrum, that is, from about 400 to about 700 nanometers.

Moreover, in a further important object of the present invention there are provided improved imaging members with extended near infrared response to, for example, 800 nanometers, and improved white light response (panchromaticity).

These and other objects of the present invention are accomplished by the provision of layered photoconductive imaging members, and more specifically imaging members comprised of thionated perylenes. In one embodiment, the layered photoconductive imaging members of the present invention are comprised of photogenerating layers, or layer comprised of thionated perylene compounds, inclusive of cis trans mixtures thereof, and in contact therewith a charge or hole transport layer or layers.

In a specific embodiment, the photoconductive layered imaging members of the present invention are comprised of, for example, a supporting substrate, an aryl hole transport layer, and thionated perylene compounds independently selected from the group consisting of those represented by the following Formulas I, II, III, and IV, illustrated in FIGS. 1 to 4, and isomers thereof wherein X is aryl, substituted aryl, arylene, heterocyclic, polycyclic aromatic components, and the like; and R is independently selected from the group consisting of hydrogen, aryl, alkyl, substituted aryl, substituted alkyl, alkoxy, aryl alkyl, aryloxy, and the like. Preferred X substituents include o-phenylene, pyridinediyl, pyrimidiinediyl, phenanthrenediyl, naphthalenediyl, and the corresponding methyl, nitro, fluoro, chloro, bromo, cyano and methoxy substituted derivatives. Preferred R substituents include hydrogen, linear and branched alkyl chains with 1 to about 25 carbons, substituted alkyl, arylalkyl, substituted aryl, a heterocyclic, and the like, such as methyl, ethyl, propyl, methoxypropyl, benzyl, phenyl, phenethyl, 4-chlorophenyl, 2-(2-pyridyl)ethyl, and the like.

Specific examples of thionated perylenes selected as the photogenerating component for the imaging members of the present invention are represented by the formulas as illustrated in FIGS. 5 to 12, wherein Pr represents propyl, that is for example bisbenzimidazole thionated perylene isomers such as cis,syn-bisbenzimidazole thionated perylene (5), cis,anti-bisbenzimidazole thionated perylene (6), transbisbenzimidazole thionated perylene (7), bispropyl thionated perylene (11), bisbenzimidazole trithionated perylene isomers such as cis,anti-bisbenzimidazole trithionated perylene (8), cis,syn-bisbenzimidazole trithionated perylene (9), trans-bisbenzimidazole trithionated perylene (10), and bispropyltrithionated perylene (12).

Figure 5:
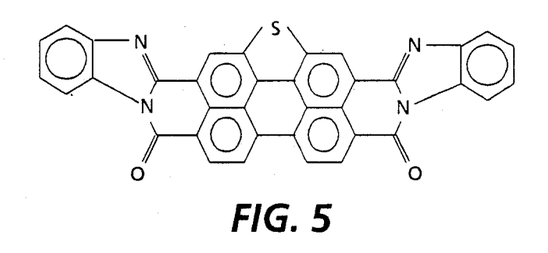
Figure 6:
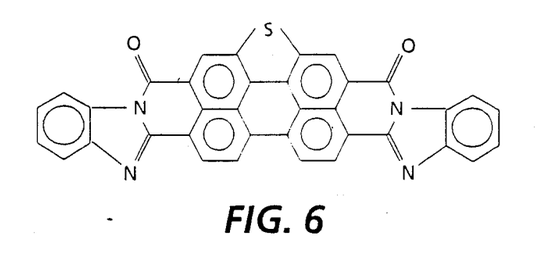
Figure 7:
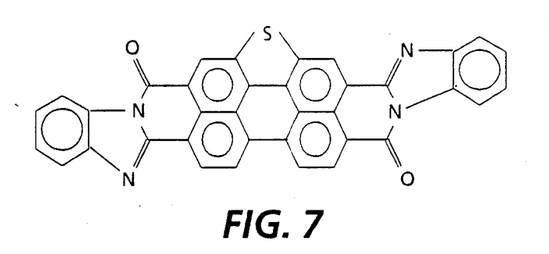
Figure 8:
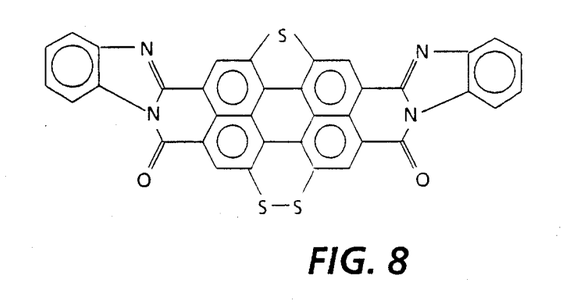
Figure 9:
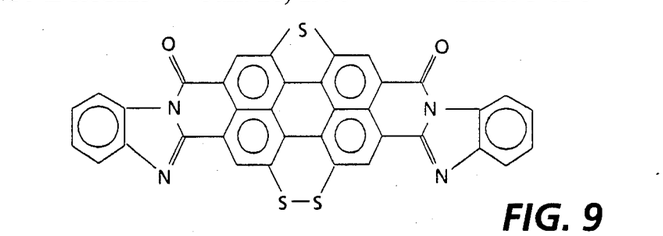
Figure 10:
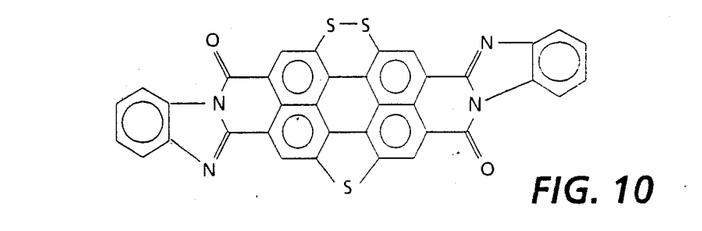
Figure 11:
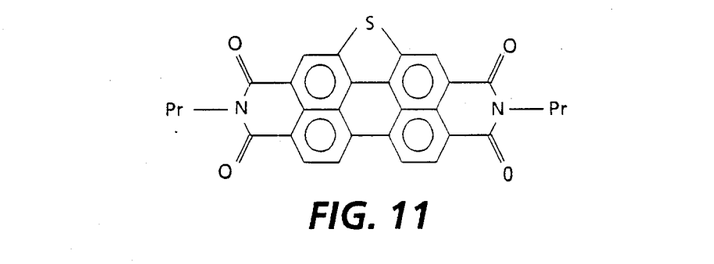
Figure 12:
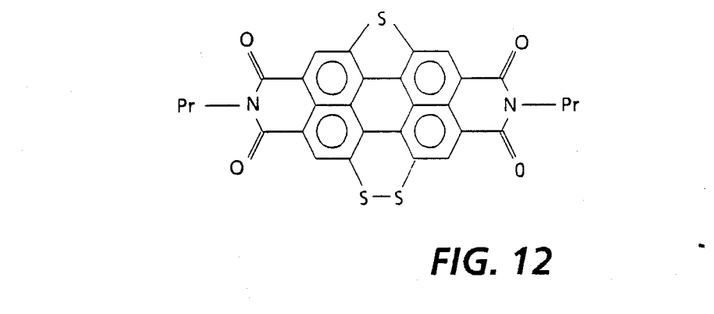

Isomer groupings include, for example, those components as represented by FIGS. 5, 6 and 7; and 8, 9 and 10. Also, geometric isomerization is possible with the components of FIGS. 1 and 3.

With further respect to the photoconductive imaging members of the present invention, the photogenerating thionated perylene compounds can be situated between the supporting substrate and the aryl amine hole transport layer; or alternatively, the aryl amine hole transport layer may be situated between the supporting substrate and the layer comprised of the photogenerating thionated perylene compounds illustrated herein. These imaging members may also include protective overcoatings thereover including polymers such as polyurethanes, polycarbonates and the like with a thickness of from about 0.2 micron to about 10 microns, or other effective thicknesses.

In another specific illustrative embodiment, the improved photoconductive imaging member of the present invention is comprised of (1) a supporting substrate; (2) a hole blocking layer; (3) an optional adhesive interface layer; (4) a photogenerating layer comprised of the thionated perylene compounds of the Formulas illustrated, and (5) a charge transport layer such as an aryl amine hole transport layer. Therefore, the photoconductive imaging member of the present invention in one important embodiment is comprised of a conductive supporting substrate, a hole blocking organo silane or siloxane or metal oxide layer in contact therewith, an adhesive layer, such as 49,000 polyester available from E. I. DuPont Chemical a photogenerating layer comprised of the thionated perylene compounds represented by the Formulas illustrated herein overcoated on the adhesive layer, and as a top layer a hole transport layer comprised of certain aryl amines dispersed in a resinous binder.

The thionated perylenes of the present invention can be prepared by the reaction of a thionated 3,4,9,10-perylenetetracarboxylic acid or the corresponding anhydride with a primary aromatic or aliphatic amine providing products of the general type illustrated by Formulas II and IV, or with an ortho- or 1,2-diamino-substituted aromatic compound or 1,8-diaminonaphthalene, which would provide structures or Formulas of the general type I and III.

Typical primary amine reactants include: ammonia, methylamine, ethylamine, propyl and isopropylamine, isomeric butylpentyl- and hexyl-amines; primary aliphatic amines with 1 to 6 carbon atoms with one or more substituents such as hydroxyl, chloro, bromo, fluoro, iodo, methoxy, ethoxy, phenoxy, methylamino, dimethylamino, nitro, thio, thiomethyl, cyano, carboxy, carboxymethyl, carboximido, and the like; aryl amines such as aniline, mono and disubstituted anilines including 4-methoxy-, 3-chloro-, 2-fluoro-, 4-dimethylamino-, 2,4-dinitroaniline, isomeric aminopyridines, aminonaphthalenes and aminosubstituted heterocyclic compounds including 2-aminothiazole, 2-aminoimidazole, and 3-amino-5-methylisoxazole; benzylamines exemplified by 4-methyl-, 4-methoxy-, 3-methoxy-, 2,4-dichloro-, 3-nitro-, and 3-methoxy-4-hydroxy-benzylamine; phenethylamines such as 2-phenethylamine and para-methoxy-, ortho-nitro-, meta-methoxy-, and para-chloro-2-phenethylamine; and heterocyclic amines such as 2-methylaminopyridine, 2-(4-pyridyl)ethylamine, and 2-(2-(1-methyl)pyrollyl)ethylamine.

Typical ortho- or 1,2-diamino-substituted aromatic diamine reactants include: ortho-phenylene diamine, 2,3-diaminonaphthalene, 2,3- and 3,4-diaminopyridine, 4,5-dimethyl-1,2-diaminobenzene, 3,4-diamino-5-hydroxypyrazole, 5,6-diamino-1,3-dimethyluracil, and the like.

The above preparation synthesis specifically involves, for example, mixing an amine or diamine with the tetracarboxylic acid or anhydride in a ratio of from about 2 to 20 moles of amine per mole of anhydride in a suitable high boiling organic solvent inclusive of dimethyl formamide, ethylene glycol, N-methyl-2-pyrrolidone, tetralin, 1-chloronaphthalene, nitrobenzene and 1,2,4-trichlorobenzene, the proportion of said solvent to the other reactants being sufficient to maintain the reaction mixture in an easily stirrable state, a ratio of from about 20 parts to 100 parts of solvent per part of anhydride being typical. The reactants are stirred and heated to a temperature of from about 120° to about 240° C. for a period of from 1 to about 20 hours which results in the addition of the amine to the anhydride and the elimination of water enabling formation of the thionated perylene. Optionally, a catalyst can be used to increase the reaction speed. Zinc compounds such as zinc iodide or zinc acetate in an amount from about 0.01 mole to 0.5 mole per mole of anhydride are particularly effective as catalysts.

The reaction mixture is then filtered while at a temperature of from about 100° to about 240° C. with a sintered glass funnel and the filtered product is washed with hot solvent, inclusive of dimethyl formamide N-methylpyrrolidone, toluene, water, nitrobenzene and tetralin at a temperature of from about 70° to about 200° C. The washing removes impurities and undesirable reaction side products formed during the reaction. The desired thionated perylene product is washed with a low-boiling solvent such as methanol or acetone and is dried in an oven at a temperature of from 60° to 150° C.

The chemical strucuture and purity of the desired thionated perylene product may be confirmed by a number of methods including infrared, $^1H$ nuclear magnetic resonance and UV-VIS-NIR spectroscopy, mass spectrometry and by elemental analysis.

In a specific embodiment of the present invention, the thionated perylenes are prepared from perylo[6,6a,6b,7-bcd]thiophene-3,4,9,10-tetracarboxylic dianhydride, and thieno[2,3,4,5-ikl] perylo[6,6a,6b,7-cde]-1,2-dithiin-4,5,9,10-tetracarboxylic dianhydride. These compounds were prepared as described in Examples I and II with adaptations of the syntheses described by V. I. Rogovik and coworkers in Organischesko Khimii 10, 1072 (1974), and Organicheskoi Khimii 22, 1050 (1986), the disclosures of which are totally incorporated herein by reference. The above compounds can be converted into the bisbenzimidazo thio derivatives, which were formed as a mixture of the three expected isomers 5, 6 and 7, and 8, 9 and 10 by treatment with ortho-phenylenediamine in refluxing N-methylpyrrolidone (NMP) solvent as described in Examples III and IV. The reaction speed can be increased by the use of catalysts such as zinc acetate and the like. The structures of the thionated perylene pigments were established by a combination of elemental analyses, high-resolution 1H nuclear magnetic resonance spectroscopy, infrared spectroscopy, mass spectrometry, and the like as indicated herein.

Various known processes can be selected for the preparation of the photoconductive imaging members of the present invention, the process parameters in the order of coating of the layers being dependent on the member desired. Specifically, for example, in one method the thionated perylene photogenerating layer is deposited on a supporting substrate by vacuum sublimation, and subsequently the hole transport layer is deposited thereover by solution coating. In another process variant, the layered photoconductive device can be prepared by providing the conductive substrate containing the hole blocking layer and an optional adhesive layer, and applying thereto by solvent coating processes, laminating processes, or other methods, the thionated perylene photogenerating layer, and the charge transport layer comprised preferably of an arylamine.

Also, in a preferred embodiment of the present invention the thionated perylene compounds of the present invention can be purified prior to incorporation in the imaging members by fractional sublimation, which involves subjecting the perylenes illustrated herein to a temperature of from about 500° to 650° C., whereby impurities and decomposition products more volatile than the desired components are separated at a temperature zone of below 200° C. There are thus obtained the desired purified perylene components at a purity of at least about 95 percent at a temperature zone of from about 290° to 460° C. separated from the nonvolatile impurities, which remain at the high temperature (500° to 650° C.) zone. The sublimation apparatus used has been described by H. J. Wagner et al. in Journal of Materials Science, Vol. 17, pp 2781 to 2791, (1982).

The improved photoconductive imaging members of the present invention can be incorporated into numerous imaging processes and apparatuses inclusive of those well known in the art such as xerographic imaging and printing processes. Specifically, the imaging members of the present invention are useful in xerographic imaging processes wherein the thionated perylene pigments absorb light of a wavelength of from about 400 nanometers to about 700 nanometers. In these processes, electrostatic latent images are initially formed on the imaging member, followed by development, and thereafter transferring the image to a suitable substrate.

BRIEF DESCRIPTION OF THE DRAWINGS

For a better understanding of the present invention and further features thereof, reference is made to the following detailed description of various preferred embodiments wherein.

DESCRIPTION OF SPECIFIC EMBODIMENTS

Specific embodiments of the present invention will now be provided with reference to specific photoconductive imaging members containing the thionated perylene compounds illustrated herein.

Figure 13:
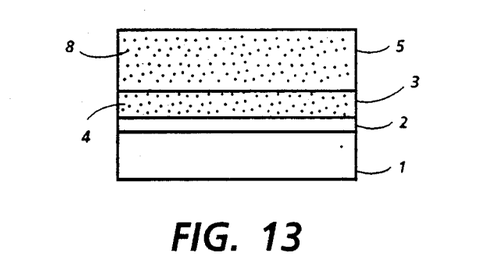
FIG. 13 is a partially schematic cross-sectional view of a photoresponsive imaging member of the present invention in which the perylene photogeneration layer is situated between a substrate and a charge transport layer.

Illustrated in FIG. 13 is a photoresponsive imaging member of the present invention comprised of a substrate 1, an adhesive layer 2, a photogenerator layer 3 comprised of a thionated perylene pigment selected from the group consisting of those represented by Formulas I, II, III, or IV, as well as mixtures thereof, and preferably bisbenzimidazole thionated perylene and bispropyl thionated perylene, respectively; optionally dispersed in a resinous binder composition 4 and a charge carrier hole transport layer 5 comprised of an aryl amine such as N,N'-diphenyl-N,N'-bis(3-methylphenyl)-[1,1'-biphenyl]-4,4'-diamine 7 dispersed in a polycarbonate resinous binder 8.

Figure 14:
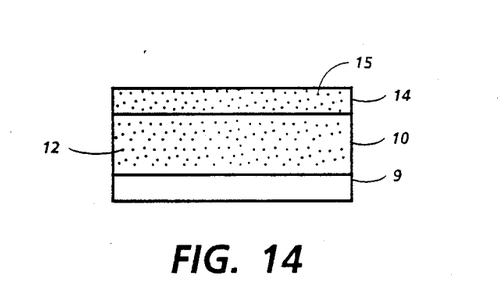
FIG. 14 is a partially schematic cross-sectional view of a photoresponsive imaging member of the present invention in which a charge transport layer is situated between a perylene photogeneration layer and a substrate.

Illustrated in FIG. 14 is a photoresponsive imaging member in which the hole transport layer is situated between the supporting substrate and the photogenerating layer. More specifically, with reference to this Figure, there is illustrated a photoconductive imaging member comprised of a supporting substrate 9, a hole transport layer 11 comprised of the aryl amine hole transport composition dispersed in an inactive resinous binder composition 12, and a photogenerating layer 14 comprised of a thionated perylene compound selected from the group consisting of those compounds represented by Formulas I, II, III or IV, and preferably the thionated perylenes of FIG. 1, optionally dispersed in a resinous binder composition 15.

Figure 15:
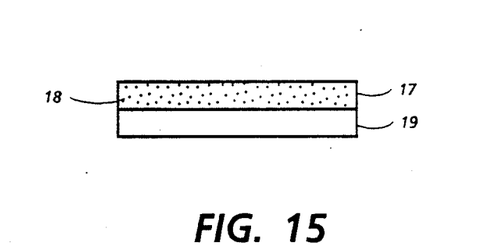
FIG. 15 is a photoresponsive imaging member of the present invention which has a perylene photogeneration and transport layer on top of a substrate.

Illustrated in FIG. 15 is a photoresponsive imaging member which is composed of a single layer 17 of a thionated perylene composition illustrated herein optionally dispersed in a resinous binder 18, and coated onto a substrate 19. Photogeneration as well as charge transport is accomplished in the single layer 17. The single layer may consist of perylene pigments with or without charge transport molecules such as aryl amines dispersed in a resinous binder composition.

Figure 1:
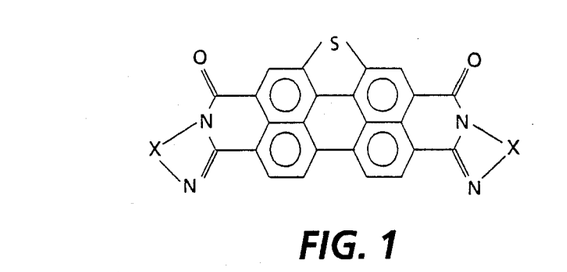
Figure 2:
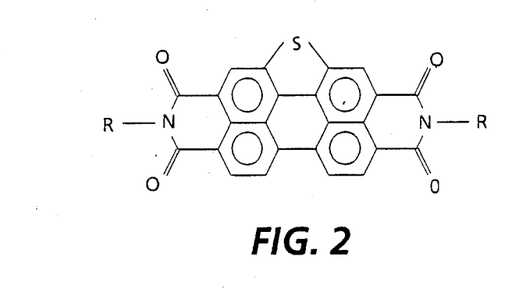
Figure 3:
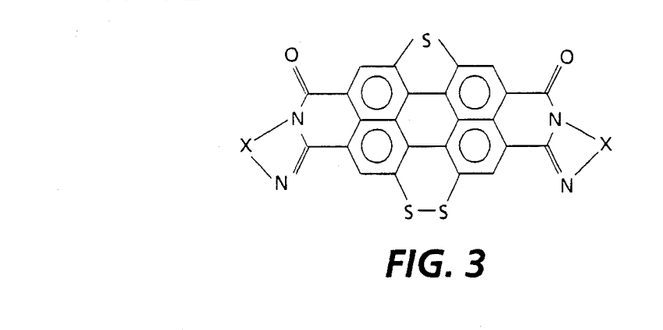
Figure 4:
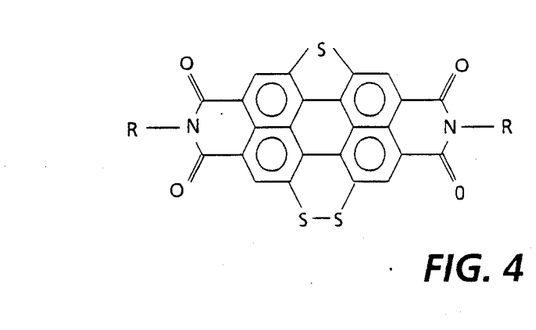
Figure 16:
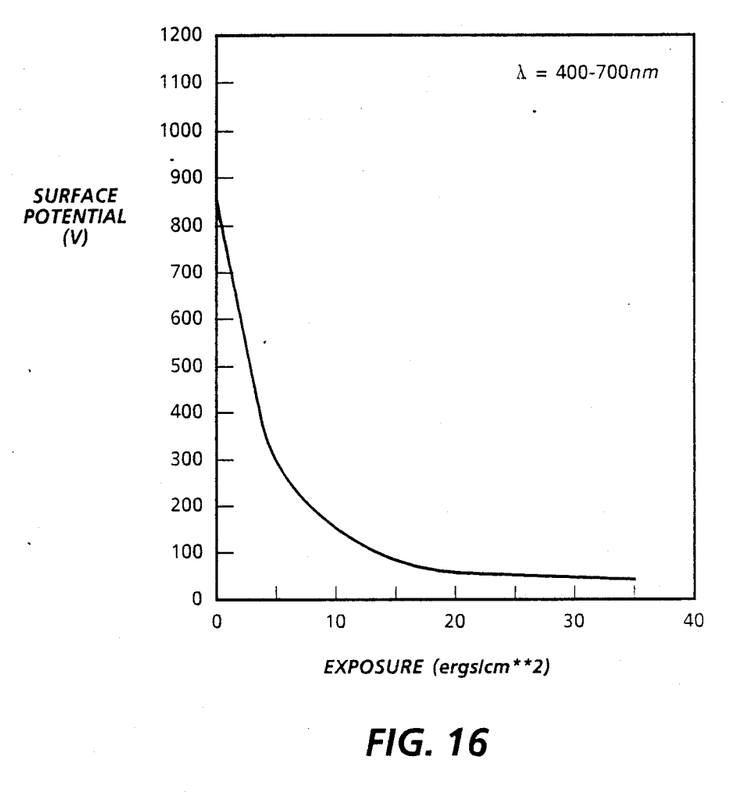
FIGS. 16 and 17 are line graphes illustrating the photosensitivity and spectral response of certain imaging members of the present invention.

FIG. 16 illustrates the photosensitivity curve for an imaging member with the bisbenzimidazole thionated perylene isomer photogenerator mixture 5, 6 and 7, the aryl amine charge transport of FIG. 1 as the top layer, and an aluminum substrate, wherein the surface potential thereof is plotted against the light exposure energies recited.

Figure 17:
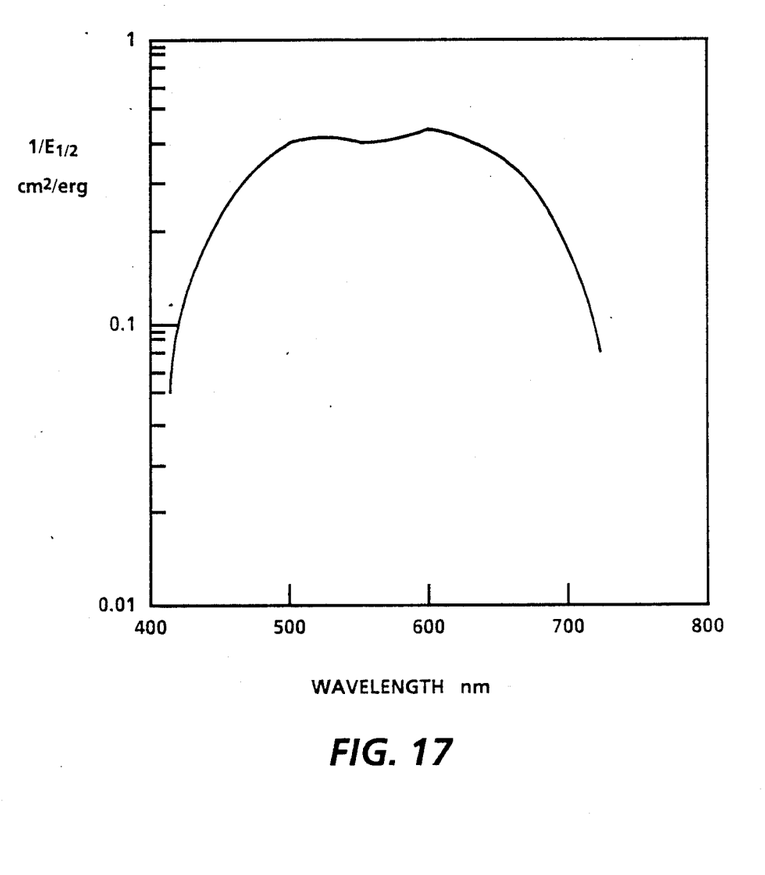

Illustrated in FIG. 17 is a spectral response plot of the 1/E½ value versus wavelength in nanometers for the photoresponsive imaging member of FIG. 13 with the bisbenzimidazole thionated perylene of FIG. 16.

With further reference to the imaging members of the present invention, the substrates may comprise a layer of insulating material such as an inorganic or organic polymeric material, including Mylar a commercially available polymer; a layer of an organic or inorganic material having a semiconductive surface layer such as indium tin oxide of aluminum arranged thereon, or a conductive material such as, for example, aluminum, chromium, nickel, titanium, brass, or the like. The substrate may be flexible or rigid and many have a number of many different configurations, such as for example, a plate, a cylindrical drum, a scroll, an endless flexible belt, and the like. Preferably, the substrate is in the form of an endless flexible belt. In some situations, it may be desirable to coat on the back of the substrate, particularly when the substrate is an organic polymeric material, an anticurl layer, such as for example, polycarbonate materials commercially available as Makrolon. The thickness of the substrate layer depends on many factors, including economical considerations, thus this layer may be of a substantial thickness, for example over 100 mils, or of minimum thickness providing there are no adverse effects on the system. In one preferred embodiment, the thickness of this layer is from about 3 mils to about 10 mils.

The optional adhesive layers are typically comprised of a polymeric material including polyesters, poly(vinyl butyral), poly(vinyl pyrrolidone), and the like. Typically, this layer is of a thickness of less than about 5 microns. The imaging member of the present invention can include other layers therein as illustrated hereinbefore, including metal oxide layers such as aluminum oxide and siloxanes, reference U.S. Pat. No. 4,464,450, the disclosure of which is totally incorporated herein by reference. Generally, the thickness of these layers is from about 0.5 to about 1 micron, however, other thicknesses can be selected providing the objectives of the present invention are achieved.

The photogenerating layers are generally of a thickness of from about 0.05 micron to about 10 microns, or more, and preferably are of a thickness of from about 0.1 micron to about 3 microns; however, the thickness of this layer is primarily dependent on the photogenerator weight loading which may vary from about 5 to 100 percent. Generally, it is desirable to provide this layer in a thickness which is sufficient to absorb about 90 percent or more of the incident radiation which is directed upon it, and the imagewise or printing exposure step. The maximum thickness of this layer is dependent primarily upon factors such as mechanical considerations, for example, whether a flexible photoconductive imaging member is desired, the thicknesses of the other layers, and the specific perylene compound selected.

Various suitable aryl amine charge transport layers can be selected for the photoconductive imaging members of the present invention, which layer has a thickness, for example, of from about 5 microns to about 75 microns, and preferably is of a thickness of from about 10 microns to about 40 microns. In a preferred embodiment, this transport layer comprises aryl amine molecules of the following formula dispersed in a highly insulating and transparent organic resinous binder wherein X is selected from the group consisting of alkyl and halogen, and preferably (ortho) CH$_3$, (meta) CH$_3$, (para) CH$_3$, (ortho) Cl, (meta) Cl, or (para) Cl.

Compounds corresponding to the above formula include, for example, N,N'-diphenyl-N,N'-bis(alkylphenyl)-[1,1-biphenyl]-4,4'-diamine wherein the alkyl is selected from the group consisting of methyl such as 2-methyl, 3-methyl, and 4-methyl, ethyl, propyl, butyl, hexyl, and the like. With halo substitution, the amine is N,N'-diphenyl-N,N'-bis(halo phenyl)-[1,1'-biphenyl]-4,4'-diamine wherein halo is 2-chloro, 3-chloro, or 4-chloro.

Examples of the highly insulating and transparent resinous material or inactive binder resinous material for the photogenerating or transport layers include materials such as those described in U.S. Pat. No. 3,121,006, the disclosure of which is totally incorporated herein by reference. Specific examples of organic resinous materials, especially for the transport layer, include polycarbonates, acrylate polymers, vinyl polymers, cellulose polymers, polyester, polysiloxanes, polyamides, polyurethanes and epoxies as well as block, random or alternating copolymers thereof. Preferred electrically inactive binder materials for the charge transport are polycarbonate resins having a molecular weight ($M_w$) of from about 20,000 to about 100,000 with a molecular weight in the range of from about 50,000 to about 100,000 being particularly preferred. Generally, the resinous binder contains from about 10 to about 75 percent by weight of the charge transport material corresponding to the foregoing formula, and preferably from about 35 percent to about 50 percent of this material. Polyvinyl carbazole is a preferred binder for the photogenerator pigment.

Also included within the scope of the present invention are methods of imaging with the photoresponsive devices illustrated herein. These methods generally involve the formation of an electrostatic latent image on the imaging member, followed by developing the image with known developer compositions, reference for example U.S. Pat. Nos. 3,590,000; 4,469,770; 4,560,635 and 4,298,672, the disclosures of which are totally incorporated herein by reference; subsequently transferring the image to a suitable substrate; and permanently affixing the image thereto.

The invention will now be described in detail with reference to specific preferred embodiments thereof, it being understood that these examples are intended to be illustrative only. The invention is not intended to be limited to the materials, conditions, or process parameters recited herein. Also, all parts and percentages are by weight unless otherwise indicated.

EXAMPLE I

Synthesis of Perylo(6,6a,6b,7-bcd) Thiophene-3,4,9,10-tetracarboxylic Dianhydride A solution of 540 grams (g) of chlorosulfonic acid, 57 g of anhydrous sodium sulfate and 57 g of perylene-3,4,9,10-tetracarboxylic dianhydride was stirred and warmed to 145° C., with an oil bath, in a 1 liter 3 necked flask fitted with a mechanical stirrer. The aforementioned solution was maintained under a positive pressure of argon while it was stirred at 145° for 16 hours. Thereafter, the solution was allowed to cool to room temperature then was slowly poured into 2,500 milliliters of a well-stirred mixture of ice and water in a 4 liter beaker. Slow careful addition was necessary since the chlorosulfonic acid hydrolysis resulting was very exothermic with violent sputtering. The resultant red suspension was filtered with a 3 liter medium porosity sintered glass funnel, and the resulting solid was washed in the funnel with deionized water until the pH of the filtrate was 4. The resultant solid was dried at 60° C. to yield 65.3 g (92 percent) of crude perylene-1,12-sulfone-3,4,9,10-tetracarboxylic acid.

The above prepared crude product was purified by dissolving 50 g of it in 800 milliliters of boiling 5 percent sodium hydroxide solution. Addition of 135 g of sodium chloride to the cooled solution caused the acid salt to precipitate, which precipitate was separated by filtration and washed in the funnel with about 100 milliliters of 15 percent aqueous sodium chloride solution. Subsequently, the product solid was then dispersed in 300 milliliters of 7 percent aqueous hydrochloric acid, and the resultant suspension was filtered and the solid product was washed with deionized water until the filtrate was neutral to pH paper. A repeat of the above purification procedure for the product afforded 25.4 g of pure perylene-1,12-sulfone-3,4,9,10-tetracarboxylic acid.

The above prepared sulfone was converted to the thionated acid compound perylo(6,6a,6b,7-bcd) thiophene-3,4,9,10-tetracarboxylic dianhydride as follows:

Sulfur (30 g, 0.94 g atom) was dissolved in 350 milliliters of boiling water containing 70 g of potassium hydroxide in a 1 liter Erylenmeyer flask. The above prepared sulfone, 30.0 g (0.65 mole) was then added to the flask and the resulting mixture was heated at reflux for 50 minutes. The resultant black solution with blue fluorescence was filtered to remove a small amount of white solid, then the solution was cooled to about 60° C. Sodium chloride (90 g) was added to the solution resulting with stirring and the resultant brown suspension was filtered using a 600 milliliters medium porosity sintered glass funnel. The resulting solid was washed in the funnel with 300 milliliters of 15 percent aqueous sodium chloride affording perylo(6,6a,6b,7-bcd) thiophene-3,4,9,10-tetracarboxylic dianhydride contaminated with some sulfur and salt.

The above prepared anhydride was purified by stirring it in 800 milliliters of boiling DMF (dimethylformamide). The anhydride initially dissolved then formed an insoluble precipitate. The suspension resulting was filtered hot and the solid product obtained was washed with 300 milliliters of boiling DMF. The solid was then washed with 250 milliliters of methanol and was dried at 60° to yield 25.0 g (82 percent) of the above thionated anhydride product, which was obtained as a 1:1 solid complex with DMF. Its structure was established using 1H nuclear magnetic resonance (nmr) spectroscopy, mass spectrometry, infrared spectrometry and elemental analysis, all of which were in accord with the proposed structure.

EXAMPLE II

Synthesis of the Thieno(2,3,4,5-ikl)perylo(6,6a,6b,7-cde)-1,2-dithiin-4,5,9,10-tetracarboxylic Dianhydride To a stirred suspension of 60 g (0.153 mole) of perylene-3,4,9,10-tetracarboxylic acid dianhydride in 1,200 milliliters of methylene chloride in a 2 liter Erlenmeyer flask was added 300 milliliters of Baker red fuming nitric acid. The acid was added dropwise over 30 minutes. Following this, the dark red suspension resulting was stirred at room temperature for 20 hours. The resultant suspension was poured over 2 liters of crushed ice in a 4 liter beaker and the product was filtered using a 1 liter, medium porosity sintered glass funnel. The solid product was washed in the funnel with 5×500 milliliters portions of deionized water (final filtrate pH=6) then with 300 milliliters of methanol. The product was dried for 20 hours at 70° C. to yield 74.8 g (94 percent) of red powder. This red powder was identified by nmr spectroscopy as a 1:1 mixture of 1,6- and 1,7-dinitro perylene-3,4,9,10-tetracarboxylic acid.

A mixture of the above prepared two dinitro compounds (20 g, 0.039 mole), and sulfur (10 g, 0.31 g atom) was stirred in 350 milliliters of NMP in a 1 liter Erlenmeyer flask. The mixture was warmed and was maintained at the reflux temperature (202°) for 10 minutes then was allowed to cool slowly to about 40° C. The black suspension resulting was filtered using a 600 milliliter medium porosity sintered glass funnel and the solid obtained was washed with DMF until the filtrate was a clear, light green color. The solid was finally washed with methanol then was dried at 70° to provide 8.15 g (44 percent) of shiny greenish black crystals, identified as the above thieno dianhydride compound by infrared, nmr spectroscopy, and by mass spectrometry.

EXAMPLE III

Synthesis of the Mixture of Bisbenzimidazole Thionated Perylene Isomers

A suspension of the 5.0 g anhydride (obtained from the process of Example I), 2.0 g of zinc acetate dihydrate and 5.0 g of orthophenylenediamine was stirred and warmed to reflux in 120 milliliters of N-methylpyrrolidone in a 250 milliliter Erlenmeyer flask on a hot plate.

The aforementioned mixture was maintained at a gentle reflux rate (195° to 202° C.) for 1 hour then was quickly cooled to 155° by the addition of cold DMF. The suspension was filtered through a 300 milliliter medium porosity sintered glass funnel which had been preheated with boiling DMF. The solid resulting was washed with 50 milliliter portions of boiling DMF until the filtrate was faintly pink in color. Thereafter, the resulting solid was washed with 50 milliliters of water then was stirred in 200 milliliters of 5 percent aqueous hydrochloric acid for 30 minutes. Filtration, washing with water then methanol, and drying at 60° for 20 hours afforded 5.83 g (87 percent) of black powder, identified by nmr spectroscopy as an approximately 2:1:1 mixture, respectively, of bisbenzimidazole thionated perylene of cis,syn-, cis,anti-, trans-isomers of FIGS. 5, 6 and 7.

EXAMPLE IV

Synthesis of the Mixture of Bisbenzimidazole Trithionated Perylene Isomers

A mixture of 4.0 g (8.3 millimole) of the anhydride (obtained by the process of Example II), 2.0 g (9.1 millimoles) of zinc acetate dihydrate, 5.0 g (46 millimoles) of ortho-phenylenediamine and 120 milliliters of NMP (N-methyl pyrrolidone) was stirred and heated to boiling (202° C.) for about 35 minutes. The resultant black suspension was allowed to cool to 155° C. then was filtered through a 350 milliliter medium porosity sintered glass funnel. The solid was washed with boiling DMF until the filtrate was colorless, then with 50 milliliters each of water and methanol. Drying at 70° C. yielded 4.92 g (90 percent) of black powder which was identified as a mixture (2:1:1, respectively) of bisbenzimidazole trithionated perylene cis,anti-, cis,syn-, trans-isomers of FIGS. 8, 9 and 10.

EXAMPLE V

Preparation of Bispropyl Thionated Perylene

A suspension of 5.0 g anhydride (obtained by the process of Example I) in a mixture of n-propylamine (10.0 g, 0.17 mole) and DMF (120 milliliters) in a 250 milliliter Erlenmeyer flask was stirred and warmed to reflux on a hot plate. The mixture began to reflux at 120° and the temperature gradually increased to 155° after 1 hour as the suspension changed from a yellow-green color to brown. Thereafter, the hot suspension was filtered through a 150 milliliters medium porosity sintered glass funnel which had been preheated with boiling DMF. The resulting solid was washed with 3×50 milliliter portions of boiling DMF until the filtrate had become a light yellow-orange color, then with 100 milliliters of methanol. Drying overnight at 60° provided 4.46 g (75 percent) of the bispropyl thionated perylene (11) as reddish-brown fibrous crystals.

EXAMPLE VI

Synthesis of the Bispropyl Trithionated Perylene

A mixture of 2.0 g (4.2 millimoles) of the anhydride (obtained from the process of Example II), and 5 g (85 millimoles) of n-propylamine was warmed to reflux in 70 milliliters of DMF in a 250 milliliters Erlenmeyer flask. The mixture was stirred at the boiling point (155°) for 1.75 hour. Thereafter, the resulting suspension was filtered at 150° using a medium porosity 350 milliliter sintered glass funnel, which had been preheated with boiling DMF and the solid was washed with boiling DMF until the filtrate became light yellow-green. The solid was then washed with methanol and was dried at 70° C. to yield 2.0 g (85 percent) of bispropyl trithionated perylene (12), a black solid having a greenish lustre identified by elemental analysis and nuclear magnetic resonance spectroscopy.

PURIFICATION OF PIGMENTS BY GRADIENT SUBLIMATION

Selected samples of thionated perylene photogenerating pigments were purified using the small-scale train-sublimation apparatus described in the Journal of Materials Science, 17, 2781 (1982), the disclosure of which is totally incorporated herein by reference. Samples were placed at the hot end of a glass tube (50 centimeters in length×25 millimeters), and nitrogen gas at a pressure of 1 millibar was allowed to pass over the sample toward the cold end. The glass tube was placed in a steel tube which was heated at one end and cooled at the other so that a temperature gradient of 200° to 300° C. formed along the length of the tube. The sublimate crystallized within a temperature zone which depended on the volatility of the pigment. Examples VII and VIII are illustrative of this general technique.

EXAMPLE VII

Train Sublimation of Bisbenzimidazole Thionated Perylene Isomers

Sublimation of a 1.47 g sample of the bisbenzimidazole thionated perylene isomers of Example III at 1 millibar using a hot zone temperature of 535° afforded 0.82 g (56 percent) of purified sublimed material as shiny gold crystals. This material condensed at a temperature of between 460° and 385° C. Spectroscopic analysis of the products evidenced no detectable impurities.

EXAMPLE VIII

Train Sublimation of Bispropyl Thionated Perylene:

A 1.75 g sample of the synthesized bispropyl thionated perylene of Example V was sublimed under conditions similar to that described in Example VII except that the hot zone temperature was 448°. The sublimate, 0.86 g (49 percent) of shiny orange-brown crystals of purified bispropyl thionated perylene, was condensed in a zone between 360° and 290°. No impurities could be detected in this material by spectroscopic analysis.

EXAMPLE IX

Photoresponsive imaging members were prepared by providing for each separate member a titanized Mylar substrate of 75 microns with a silane layer (gamma-aminopropyl methyl diethoxysilane), 0.1 micron in thickness thereover, a polyester adhesive layer thereon in a thickness of 0.1 micron, and depositing thereover with a Balzers vacuum coater a photogenerating layer of thionated perylene pigments. The photogenerating pigments selected were the bisbenzimidazole thionated perylene pigments of Examples III and VII and the bispropyl thionated perylene of Example V, respectively. The photogenerating layer had a final thickness of 0.2 micron. More specifically, each of the photogenerator components were evaporated from an electrically heated tantalum boat and the vacuum coater was evacuated to a pressure of $10^{-5}$ Torr. Each of the photogenerator layers were deposited at a rate of 1 to 4 Angstroms/second on the adhesive layer.

Thereafter, the above photogenerator layers present in the respective imaging members were each overcoated with an amine charge transport layer prepared as follows: A transport layer mixture with 65 percent by weight Makrolon, a polycarbonate resin, was mixed with 35 percent by weight N,N'-diphenyl-N,N'-bis(3-methyl-phenyl)-[1,1'-biphenyl]-4,4'-diamine, and 13.5 percent by weight in methylene chloride in an amber bottle. The resulting mixture was then coated onto the above photogenerator layers using a multiple clearance film applicator (10 mils gap). The resulting members were then dried at 135° C. for 20 minutes. The transport layer thus obtained had a thickness of 20 microns.

The xerographic electrical properties of the aforementioned imaging members were then determined by electrostatically charging the surfaces thereof with a corona discharge source until the surface potentials, as measured by a capacitively coupled probe attached to an electrometer, attained an initial value $V_o$ of about −800 volts. After resting for 0.5 second in the dark, the charged members reached a surface potential of $V_{ddp}$, dark development potential, and each member was then exposed to light from a filtered Xenon lamp with a XBO 150 watt bulb. A reduction in surface potential to a $V_{bg}$ value, background potential, due to photodischarge effect was observed. The dark decay in volt/second was calculated as $(V_o\text{-}V_{ddp})/0.5$. The percent of photodischarge was calculated as 100 percent $(V_{ddp}\text{-}V_{bg})/V_{ddp}$. The desired wavelength and energy of the expose light was determined by the type of filters placed in front of the lamp. The broad band white light (400 to 700 nanometers) photosensitivity of these imaging members was measured by using an infrared cut-off filter whereas the monochromatic light photosensitivity was determined using a narrow band-pass filter.

The photosensitivity of the imaging members is usually provided in terms of the amount of expose energy in erg/cm², designated as $E_½$, required to achieve 50 percent photodischarge from the dark development potential. The higher the photosensitivity, the smaller is the $E_½$ value.

Table 1 summarizes the xerographic electricals of the aforementioned imaging members. The dark decay and white light photosensitivity values are listed.

TABLE 1

| Imaging Member | Perylene Photogenerator | Purification Method | Dark Decay V/s | $E_½$ erg/cm² |
|---|---|---|---|---|
| 1 | bisbenzimidazole thionated perylene Example VII | sublimation | 8 | 4.0 |
| 2 | bisbenzimidazole thionated perylene Example III | solvent washed | 18 | 6.5 |
| 3 | bispropyl thionated perylene Example V | solvent washed | 7 | 48.0 |

These imaging members possess low dark decay values as indicated. The imaging member with bisbenzimidazole thionated perylene evidences higher photosensitivity than bispropyl thionated perylene. For the bisbenzimidazole compound, sublimation can further improve the photosensitivity over solvent purification.

The white light photosensitivity result for the bisbenzimidazole thionated perylene member (Imaging Member 1) is further illustrated in FIG. 16 where the percent photodischarge is plotted against various exposure energies.

To obtain the spectral response of the imaging members, $E_½$ values were determined at various monochromatic wavelengths. The spectral response curve of the bisbenzimidazole thionated perylene member 1 is depicted in FIG. 17 where the $E_½$ values are plotted against wavelength. The device shows a broad spectral response from 400 to 700 nanometers.

The cyclic stability of the same bisbenzimidazole thionated perylene member was investigated by a repetitive charging and photodischarging process for 1,000 times. The changes in surface potentials $V_o$, $V_{ddp}$ and $V_{bg}$ remained very small, <30 volts, indicating that the member had an excellent stability for xerographic applications.

EXAMPLE X

PHotoresponsive imaging members containing a photogenerator layer which was prepared from solution coating of a pigment dispersion were fabricated. The pigment dispersion was prepared as follows: 0.40 gram of the perylene pigment of Table 2 was mixed with 0.1 gram of polyvinylcarbazole (PVK) polymer in a 30 cc glass bottle containing 70 grams of ⅛ inch stainless steel shots and 10.72 grams of methylene chloride. The bottle was placed on a roller mill and the dispersion was milled for 24 hours. The pigment dispersions were coated onto a titanium metallized Mylar substrate in a thickness of 75 microns using a film applicator of 1.5 mil gap. Thereafter, the photogenerator layers formed were dried in a forced air oven at 135° C. for 20 minutes. Perlyene pigments prepared according to Examples III, V and VI were selected and for each pigment a photogenerator layer was deposited in the aforementioned manner.

The amine charge transport layers were then coated onto the above prepared photogenerator layers as described in Example IX.

The xerographic electrical properties of the photoresponsive members were tested according to the procedure of Example IX. The white light (400 to 700 nanometers) photosensitivity results obtained are summarized in Table 2.

For xerography applications, thionated perylene pigments (Imaging Members 4 and 5) appear to be superior to the trithionated perylene (Imaging Member 6) since, for example, members 4 and 5 possess a lower dark decay and higher photosensitivity.

TABLE 2

| Device No. | Perylene Photogenerator | Purification Method | Dark Decay V/s | $E_{\frac{1}{2}}$ erg/cm$^2$ |
|---|---|---|---|---|
| 4 | bisbenzimidazole thionated perylene Example III | solvent washed | 22 | 11 |
| 5 | bispropyl thionated perylene Example V | solvent washed | 17 | 22 |
| 6 | bispropyl trithionated perylene Example VI | solvent washed | 70 | 76 |

Other modifications of the present invention may occur to those skilled in the art subsequent to a review of the present application, and these modifications are intended to be included within the scope of the present invention.

What is claimed is:

1. A photoresponsive imaging member comprised of a thionated perylene photogenerator layer, and a charge transport layer.

2. A photoconductive imaging member comprised of a supporting substrate, a thionated perylene photogenerating layer, and a charge transport layer.

3. An imaging member in accordance with claim 2 wherein the thionated perylene is of the Formulas as represented by FIGS. 1, 2, 3, or 4, wherein x is aryl, heterocyclic, polycyclic arylenes, and the substituted derivatives thereof; R is hydrogen, alkyl, aryl, aryl alkyl, alkoxyalkyl, and the substituted derivatives thereof.

4. An imaging member in accordance with claim 3 wherein aryl contains from 6 to about 24 carbon atoms.

5. An imaging member in accordance with claim 3 wherein alkyl contains from 1 to about 25 carbon atoms.

6. An imaging member in accordance with claim 2 wherein the thionated perylene is cis,syn-, cis,anti-, and trans-bisbenzimidazole thionated perylenes, bispropyl thionated perylene, cis,anti-, cis,syn-, and trans-bisbenzimidazole trithionated perylenes, or bispropyl trithionated perylene.

7. An imaging member in accordance with claim 2 wherein the photogenerating layer is situated between the supporting substrate and the charge transport layer.

8. An imaging member in accordance with claim 2 wherein the aryl amine hole transport layer is situated between the supporting substrate and the photogenerating layer.

9. An imaging member in accordance with claim 2 wherein the charge transport layer is an aryl amine.

10. An imaging member in accordance with claim 2 wherein the supporting substrate is comprised of a conductive metallic substance, or an insulating polymeric composition overcoated with an electrically conductive layer.

11. An imaging member in accordance with claim 10 wherein the supporting substrate is aluminum, an organic polymeric composition, aluminized Mylar or titanized Mylar.

12. An imaging member in accordance with claim 2 wherein the photogenerating thionated perylene is dispersed in a resinous binder in an amount of from about 5 percent by weight to about 95 percent by weight.

13. An imaging member in accordance with claim 12 wherein the resinous binder is a polyester, poly(vinylbutyral), polycarbonate, poly(vinylformal), poly(vinylcarbazole), poly(vinylchloride), or mixtures thereof.

14. An imaging member in accordance with claim 2 wherein the charge transport layer is comprised of aryl amine molecules of the formula dispersed in a highly insulating and transparent organic resinous binder wherein X is selected from the group consisting of alkyl and halogen.

15. An imaging member in accordance with claim 14 wherein X is selected from the group consisting of ortho (CH$_3$), meta (CH$_3$), para (CH$_3$), ortho (Cl), meta (Cl), or para (Cl).

16. An imaging member comprised of (1) a supporting substrate; (2) a siloxane hole blocking layer; (3) a photogenerating layer comprised of the thionated perylene compounds of the Formulas of FIGS. 5, 6, 7, 8, 9, 10, 11, or 12 wherein Pr is propyl; or the Formulas of FIGS. 1, 2, 3 or 4 wherein x is aryl, heterocyclic, polycyclic arylenes, and the substituted derivatives thereof; R is hydrogen, alkyl, aryl, aryl alkyl, alkoxyalkyl, and the substituted derivatives thereof; and (4) an aryl amine hole transport layer.

17. An imaging member in accordance with claim 16 wherein there is included between the siloxane hole blocking layer and the photogenerating layer an adhesive layer.

18. An imaging member in accordance with claim 17 wherein the adhesive layer is a polyester resin.

19. An imaging member in accordance with claim 16 wherein the charge transport comprises aryl amine molecules of the formula wherein X is selected from the group consisting of alkyl and halogen.

20. A method of imaging or printing which comprises generating an image on the imaging member of claim 1; developing the image generated; transferring the developed image to a suitable substrate; and thereafter affixing the image thereto.

21. An imaging member in accordance with claim 3 wherein the thionated perylene is of the formulas of FIGS. 5, 6, 7, 8, 9, 10, 11 or 12, isomers thereof, or mixtures thereof, wherein Pr is propyl.

22. An imaging member in accordance with claim 3 wherein the photogenerating thionated perylene is deposited by vacuum evaporation.

23. A photoconductive imaging member comprised of a thionated perylene photoconductive layer which functions as a photogenerator and as a charge transport, which layer is deposited on a supporting substrate.

24. An imaging member in accordance with claim 23 wherein the thionated perylene is of the Formulas of FIGS. 1, 2, 3 or 4, isomers thereof, or mixtures thereof; FIGS. 5, 6, 7, 8, 9, 10, 11 or 12, isomers thereof, or mixtures thereof, wherein x is aryl, heterocyclic, polycyclic arylene, or the substituted derivatives thereof; R is hydrogen, alkyl, aryl, aryl alkyl, alkoxyalkyl, or the substituted derivatives thereof; and wherein Pr is propyl.

25. An imaging member in accordance with claim 3 wherein X is o-phenylene, pyridinediyl, pyrimidinediyl, phenanthrenediyl, naphthalenediyl, or the corresponding alkyl, nitro, halo, cyano, and methoxy substituted derivatives.

26. An imaging member in accordance with claim 21 wherein the thionated perylene is comprised of an isomer mixture of the formulas as represented by FIGS. 5, 6 and 7, or 8, 9 and 10 wherein Pr is propyl.

27. An imaging member in accordance with claim 2 wherein the thionated perylene is of the Formulas as represented by FIGS. 1, 2, 3, or 4, or mixtures thereof wherein x is aryl, heterocyclic, or polycyclic arylenes; and R is hydrogen, alkyl, aryl, aryl alkyl, alkoxyalkyl, or the substituted derivatives thereof.

28. An imaging member in accordance with claim 2 wherein the thionated perylene is of the Formulas as represented by FIGS. 5, 6, 7, 8, 9, 10, 11, or 12, mixtures thereof, or isomers thereof wherein Pr is propyl.

29. An imaging member in accordance with claim 3 wherein the perylene is comprised of mixtures, or isomers of the thionated compounds represented by FIGS. 1, 2, 3 or 4 wherein x is aryl, heterocyclic, polycyclic arylenes, and the substituted derivatives thereof; R is hydrogen, alkyl, aryl, aryl alkyl, alkoxyalkyl, and the substituted derivatives thereof.

30. An imaging member in accordance with claim 16 wherein the perylene is comprised of mixtures, or isomers of the thionated compounds represented by FIGS. 5, 6, 7, 8, 9, 10, 11 or 12 where Pr is propyl.

* * * * *